United States Patent [19]

Ritter

[11] Patent Number: 4,888,487
[45] Date of Patent: * Dec. 19, 1989

[54] TOOTHBRUSH STERILIZER WITH AUTOMATIC CONTROL

[76] Inventor: Charles H. Ritter, 3219 Thomasville Rd., #17A, Tallahassee, Fla. 32312

[*] Notice: The portion of the term of this patent subsequent to Feb. 7, 2006 has been disclaimed.

[21] Appl. No.: 306,566

[22] Filed: Feb. 6, 1989

Related U.S. Application Data

[63] Continuation of Ser. No. 21,252, Mar. 3, 1987, Pat. No. 4,803,364.

[51] Int. Cl.⁴ ............................................. A61L 3/00
[52] U.S. Cl. ........................... 250/455.1; 250/504 R; 422/24
[58] Field of Search ............... 250/455.1, 453.1, 454.1, 250/504 R; 422/24

[56] References Cited

U.S. PATENT DOCUMENTS

| | | | |
|---|---|---|---|
| D. 223,874 | 6/1972 | Ellis | D83/1 |
| 2,180,213 | 11/1939 | Peake | 312/207 |
| 2,245,762 | 6/1941 | Stefani et al. | 250/455.1 |
| 2,246,135 | 6/1940 | James | 250/455.1 |
| 2,350,091 | 5/1944 | Bergman | 250/455.1 |
| 2,554,152 | 5/1951 | Rosenthal | 250/455.1 |
| 2,579,242 | 12/1951 | Pask | 250/455.1 |
| 2,587,131 | 2/1952 | Ficken | 250/455.1 |
| 2,592,131 | 4/1952 | Farrar | 250/455.1 |
| 3,748,094 | 7/1973 | Scheidell | 21/83 |
| 3,776,694 | 12/1973 | Leittl | 21/102 R |
| 3,820,251 | 6/1974 | Abernathy | 34/60 |
| 3,906,236 | 9/1975 | Callahan | 250/455.1 |
| 3,954,407 | 5/1976 | Audary et al. | 21/83 |
| 4,088,445 | 5/1978 | Ellis | 21/83 |
| 4,412,134 | 10/1983 | Herold et al. | 250/504 R |
| 4,625,119 | 11/1986 | Murdock, III | 250/455.1 |
| 4,740,706 | 4/1988 | Murdock, III | 250/455.1 |
| 4,803,364 | 2/1989 | Ritter | 250/504 R |
| 4,806,770 | 2/1989 | Hylton et al. | 250/455.1 |

Primary Examiner—Carolyn E. Fields
Assistant Examiner—John A. Miller
Attorney, Agent, or Firm—Shlesinger & Myers

[57] ABSTRACT

A toothbrush conditioner includes a body having an upper end. A cover member is removably mounted to the upper end for therewith providing a conditioning chamber. A support plate is positioned within the body member for selectively positioning a toothbrush to be conditioned within the chamber. An ultraviolet radiation source is carried by the cover member and is movable therewith for being selectively positioned within the chamber proximate the brush to be conditioned when the cover member is mounted to the upper end. A plurality of vent openings are in the body member. A control device is in connection with the radiation source for causing selective intermittent operation thereof.

27 Claims, 3 Drawing Sheets

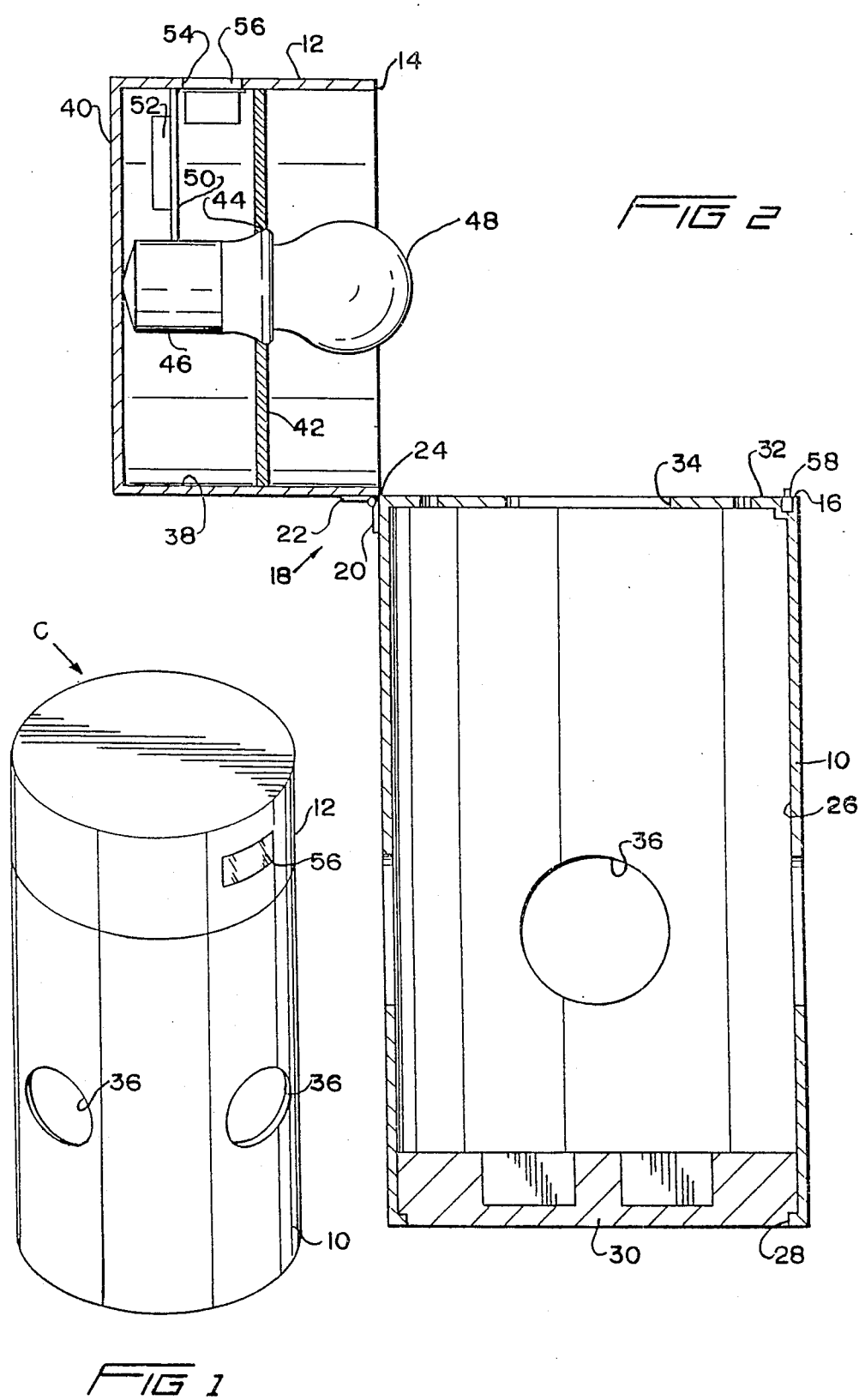

TOOTHBRUSH STERILIZER WITH AUTOMATIC CONTROL

This is a continuation of application Ser. No. 021,252, now U.S. Pat. No. 4,803,364, filed Mar. 3, 1987.

BACKGROUND OF THE INVENTION

An intern virus may remain alive on a countertop for up to several hours, thereby permitting those who come into contact with the countertop to run the risk of infection. Also, many people have frequent bleeding from the gums, which can otherwise transfer blood and contaminants therein to the toothbrush which they use. It is common for the user of a toothbrush, particularly when at the work place, to leave the brush is a publicly accessible place, such as on a restroom countertop or the like. In that location, the toothbrush is then capable of being contaminated by any local intern virus, as well as free to be contaminated by insects and the like, or may itself contaminate the countertop.

The prior art discloses a number of devices for sterilizing or otherwise conditioning a toothbrush by means of radiant energy. The most common radiant energy source is an ultraviolet lamp. Ultraviolet radiation is used because of its sterilizing effect. Ultraviolet radiation produces a violent vibration in the cell walls of microbes, causing them to rupture and kill the organism.

Two basic types of ultraviolet toothbrush conditioners are known. The first operates continuously, thereby acting more as a still than a sterilizer. The other type operates in an on-off way, thereby running the risk that the brush is not properly conditioned before a subsequent use. Neither of these types appreciates the problem of vapor condensation at the top of the device, which condensation provides a source for continued contamination.

In view of the above, it can be seen that there is a need for a toothbrush conditioner which effectively destroys contaminating microbes and the like by bombardment with radiant energy of a selected wavelength. Preferably, the conditioner optimally balances the relevant thermodynamic relationships to assure that the vapor is driven away from the brush so as to exit the device, thereby drying the bristles and avoiding subsequent contamination through condensation. The disclosed invention is just such a conditioner and satisfactorily avoids the problems of the prior art.

OBJECTS AND SUMMARY OF THE INVENTION

The primary object of the disclosed invention is to provide an ultraviolet wavelength toothbrush conditioner which has optimum thermodynamic design in order to drive the moisture away from the bristles and out of the conditioning chamber.

The toothbrush conditioning device of the invention includes a body member having an upper end. A cover member is removably mounted to the upper end and forms with the body member a conditioning chamber. A plate is mounted in the body member for selectively positioning within the chamber a toothbrush to be conditioned. An ultraviolet radiation source is carried by the cover member and is movable therewith so that the source is selectively positioned within the chamber proximate a brush or brushes to be conditioned when the cover member is mounted to the upper end. A plurality of openings are in the body member for permitting water vapor to vent from the chamber. A programmable timer and switch mechanism are provided for intermittently operating the radiant source for a selected period when the cover member is mounted to the upper end.

These and other objects and advantages of the invention will be readily apparent in view of the following description and drawings of the above described invention.

DESCRIPTION OF THE DRAWINGS

The above and other object and advantages and novel features of the present invention will become apparent from the following detailed description of the preferred embodiment of the invention illustrated in the accompanying drawings, wherein:

FIG. 1 is a perspective view illustrating my toothbrush conditioner;

FIG. 2 is a longitudinal cross-sectional view thereof with the cover member shown in the pivoted position;

DESCRIPTION OF THE INVENTION

Figure 3:
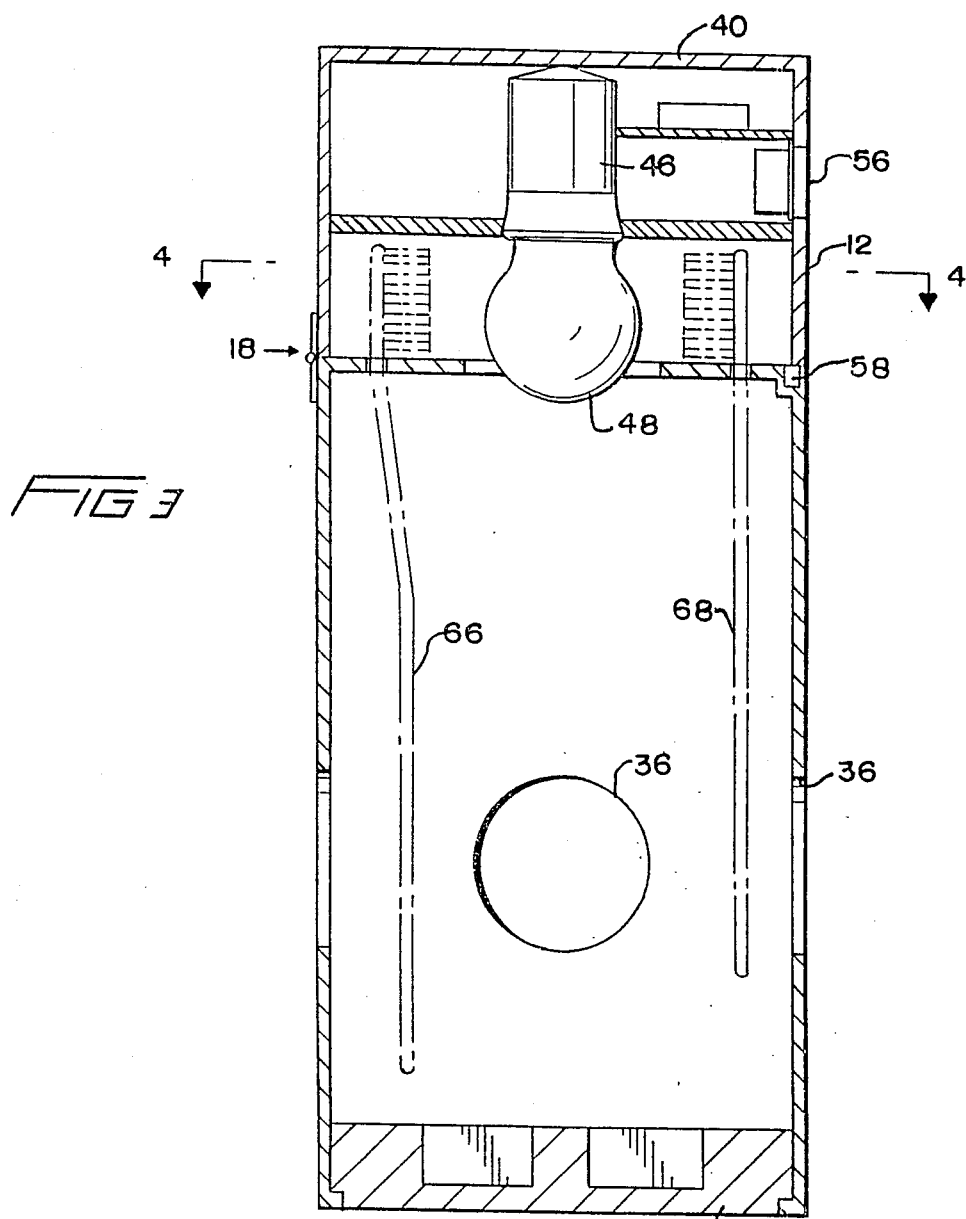
FIG. 3 is a cross-sectional view with the cover member shown in the closed position, and with toothbrushes shown in phantom lines.

Conditioner C, as best shown in FIGS. 1-3, is a cylindrical device, although other configurations may be appropriate in certain instances. The conditioner C includes a body member 10 and a cover member 12. Preferably, the body and cover members 10 and 12, respectively, have a uniform diameter so that the lower edge 14 of the cover member 12 seats with the upper end edge 16 of body member 10. It is to be noted in FIGS. 2 and 3 that the body member 10 has a length substantially in excess of the length of cover member 12, the body member 10 having a length substantially corresponding to the length of a toothbrush. Each of the body and cover members 10 and 12, respectively, is comprised of an opaque plastic material, although other materials and coloring may be appropriate. I prefer an opaque material for the exterior of the condition C in order to minimize any hazard which could occur from exposure to ultraviolet radiation.

Hinge 18 has a first leaf 20 secured to body member 10 and a second leaf 22 secured to cover member 12. Naturally, the hinge 18 includes a pivot pin 24 to permit the cover and body members 12 and 10, respectively, to pivot relative to each other, and the pivot pin 24 is aligned with the upper edge 16 of the body member 10. In this way, the cover member 12 may be pivoted from the closed position illustrated in FIG. 3, to the open position illustrated in FIG. 2.

Body member 10 has a central aperture 26 therethrough which is closed at lower end 28 by member 30. The member 30 may be used for supporting the conditioner C on a countertop, or the like. Support plate 32 extends across upper end edge 16 and has a central aperture 34 for reasons to be explained. Preferably, the support plate 32 is integral with or secured to body member 10. The plate 32 may be comprised of an opaque plastic, although a clear plastic is preferred for increased conditioning effect within the body chamber. Body member 10 also includes a plurality of vent openings 36, as will be further explained.

Cover member 12 has an aperture 38 therethrough which is closed by top member 40. In this way, pivoting of the cover member 12 into the closed position of FIG. 3 provides a conditioning chamber in cooperation with the body member 10.

A support member 42 extends parallel to top member 40 and is disposed intermediate lower edge 14 and top member 40. Support member 42 includes an aperture 44 therethrough in which socket 46 is secured. Ultraviolet lamp 48 is removably secured in socket 46, in a manner well known in the art. The socket 46 is centrally positioned relative to cover member 12 so that the lamp 48 is likewise centrally positioned.

Secondary support 50 extends from socket 46 to the wall of cover member 12 above support member 42. Control device 52, which may include a modern electronic control mechanism, is mounted to secondary support 50. The conventional wiring and connections for the control device 52 are omitted for the sake of clarity. Control device 52 is positioned within cover member 12 in order to minimize the wire lengths and increase compactness.

Opening 54 is disposed in the side wall of member 12, and is disposed between secondary support 50 and support member 42. Display 56 is positioned in opening 54 and is in operative connection with control device 52 by means not shown. Display 56 preferably includes a digital clock or the like, in order to facilitate programming of the control device 52.

FIGS. 2 and 3 disclose switch assembly 58 which extends axially upwardly from the side wall of body member 10. The switch assembly 58 is aligned with lower edge 14 and is engageable therewith when the cover member 12 is in the closed position of FIG. 3. The switch assembly 58 is in operative connection, by means not shown, with the control device 52. Engagement of the lower edge 14 with the switch assembly 58 indicates to the control device 52 that the cover member 12 is in the closed position, thereby permitting the lamp 48 to be operated at the appropriate time, as will be further explained. Naturally, switch assembly 58 could just as easily extend from edge 14.

Figure 4:
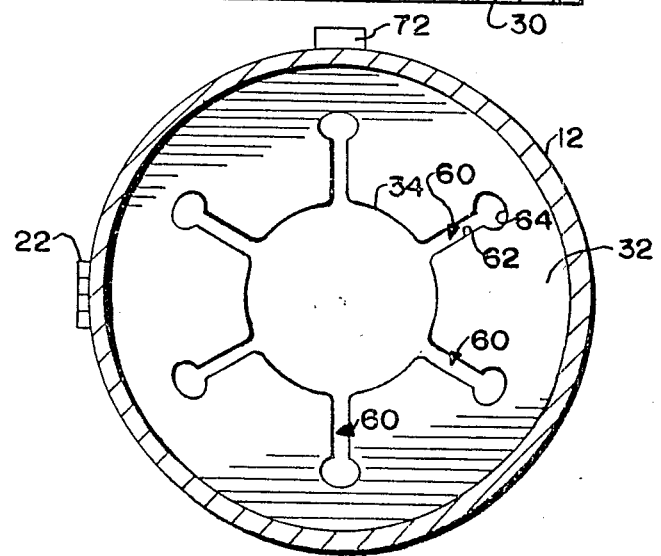
FIG. 4 is a cross-sectional view taken along the section 4—4 of FIG. 3, and viewed in the direction of the arrows, and with the toothbrushes omitted for the sake of clarity.

FIG. 4 discloses slots 60 extending radially from central aperture 34 in support plate 32. Each of the slots 60 extends through the support plate 32 and includes a relatively straight portion 62 and an oval enlarged portion 64. The slots 60 communicate with the central aperture 34 in order to permit a toothbrush, such as the toothbrushes 66 and 68 of FIG. 3 to be supported by the support plate 32.

Each of toothbrushes 66 and 68 is aligned for insertion with the respective portion 62 and is moved radially therealong until the toothbrush may be rotated upon being positioned within the enlarged portion 64. A typical toothbrush, such as 66 or 68, has a bristle-carrying head. The neck has a reduced width. The enlarged area 64 has a diameter less then the width of the head, so that the head will rest upon the adjacent portions of the plate 32 and thereby be maintained at the proper positioning for further conditioning. This prevents the bristles from resting upon the plate and becoming bent. Removal of the toothbrush from the enlarged portion 64 merely requires that the brush be rotated and then slid through the respective straight portion 62 until the opening 34 is reached, thereby permitting removal.

Figure 5:
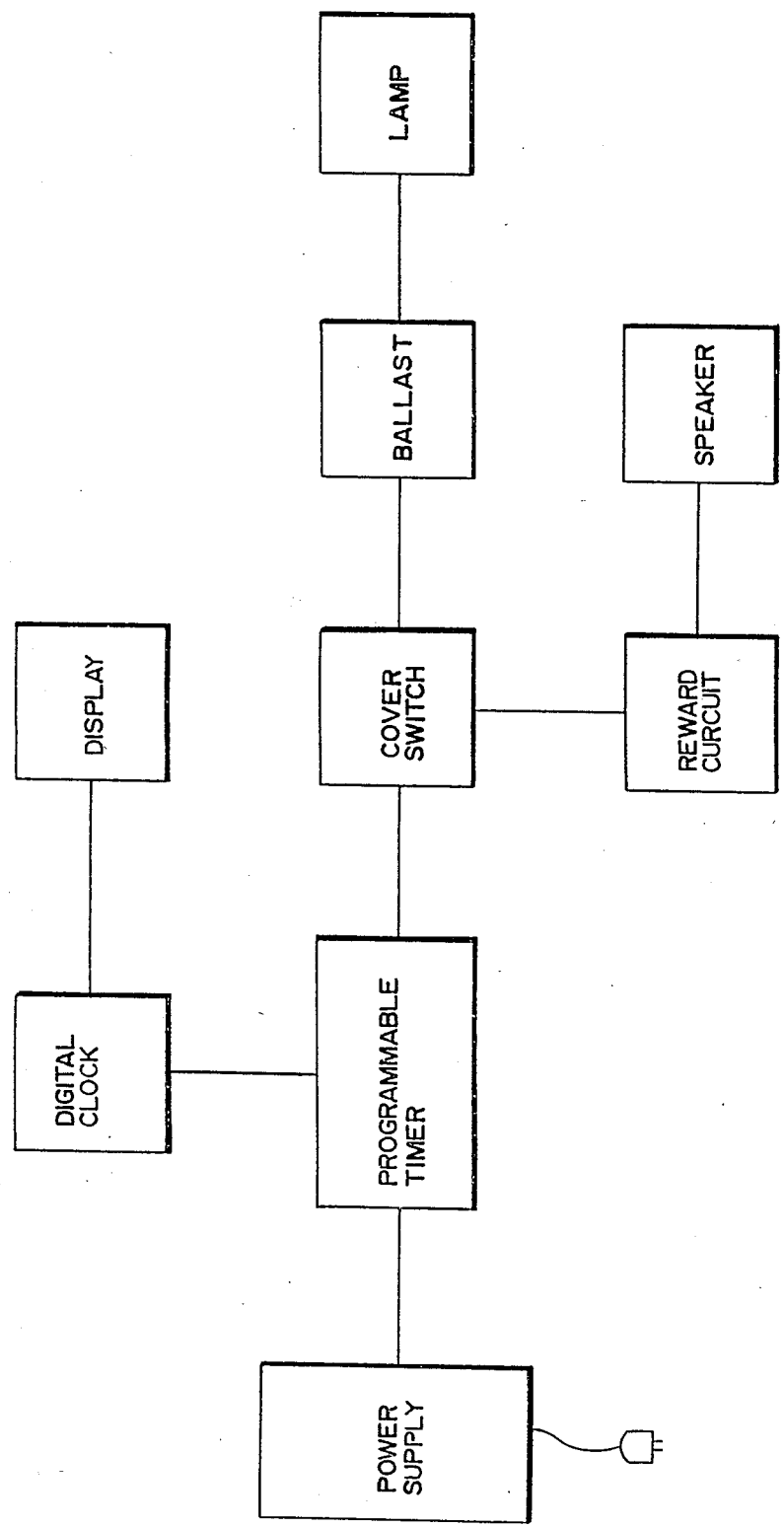
FIG. 5 is an elementary schematic view of the control circuitry of the invention.

FIG. 5 discloses an elementary schematic diagram illustrating the control circuit of the invention as provided by the control device 52 and the related assemblies. A power supply has an electric cord with a plug for permitting connection with a source of electric power. Although a plug 70 is illustrated in FIG. 5, those skilled in the art will understand that a battery source is also possible. The power supply includes the appropriate voltage and current regulating devices as may be required.

The power supply is connected with a programmable timer which causes the lamp 48 to be operated for a preselected duration upon the passage of a selected interval. As noted, I have found that continuous operation of the conditioner C is not required, it merely being necessary for the lamp 48 to operate for the appropriate period of time required to destroy the contaminants. Intermittent operation is desirable in order to avoid the humidor-like effects that can occur from continuous operation. Intermittent operation of the lamp 48 also assures that the bristles of the toothbrush are not prematurely degraded by the conditioning effects of the ultraviolet radiation.

A cover switch, such as the switch assembly 58, is in operative connection with the programmable timer and permits the lamp 48 to be operated only when the cover member 12 is in the closed position. The cover switch therefore prevents the user from being exposed to the ultraviolet radiation should the cover member 12 be lifted during a burn cycle. The ballast for the lamp 48 is likewise in connection with the cover switch and is of a type well-known in the art.

The programmable timer is also connected with a digital clock in order to display the time to the user through the display 56. The display 56 therefore avoids the need for a bathroom clock, and also permits the user to set the programmable timer when the conditioner C is initially installed.

FIG. 5 also discloses a reward circuit and an audio speaker which may be appropriate in a conditioner C directed for use by children. The reward circuit generates some sort of audio encouragement to the child user upon his use of the conditioner C, as well as of the appropriate toothbrush. The prior art discloses certain forms of audio synthesis techniques, such as by computer chips and the like, which can be easily adapted for use with the circuit of FIG. 5. It is well-known that it is difficult to get children to use their toothbrush on a regular basis, and the reward circuit will therefore increase a child's use, as well as make sure that he uses a properly conditioned toothbrush.

I have designed the conditioner C in order to obtain drying of the toothbrush, while also achieving reduction, essentially elimination, of interchamber condensation. The thermodynamic design of the conditioner C is such that the hottest point in the chamber is at the highest point. Naturally, the lamp 48 provides this hot point and, because of its location adjacent the support member 42, is appropriately arranged for maximizing the temperature at the upper end of th chamber. Because the hottest point is at the highest point in the chamber, a downward flow of the moisture laden vapor from the toothbrush is caused to occur. This downward moisture flow communicates through the straight portions 62 and the central aperture 34, until the moisture exits through the vent openings 36. The vent openings 36 are relatively large in order to create a draft for vapor removal, thereby preventing the moisture laden vapor from condensing on the bottom of support member 42.

I have found that there is minimal risk of brush contamination from ambient room air, particularly when the cover member 12 is in the closed position. Furthermore, a finite period is required for colonization of the bristles after contamination and intermittent operation of the lamp 48 is set to occur frequently enough to prevent this colonization. Therefore, any ambient contamination is destroyed before subsequent use. Furthermore, although I disclose that the lower end 28 of the body member 10 is closed by member 30, this is not necessary and an open end further reduces the risk of condensation contamination. Also, an open end more easily permits the interior of the conditioner C to be cleaned.

I prefer that the lamp 48 be of the globe-like configuration in order to provide substantially uniform radiation of the surrounding toothbrushes. Furthermore, the lamp 48 is carried by the cover member 12 in order to pivot the lamp 48 away from the cover plate 32 when a toothbrush is being inserted or removed from the conditioner C. In this way, the risk of a wet brush contacting a hot lamp 48 is minimized, thereby avoiding permature lamp failure or even breakage. It is to be noted in FIG. 3 that the lamp 48 extends through the central aperture 34 in order to make sure that the air within the body member 10 is heated and driven through the vent openings 36, and that the brush handle is conditioned by the radiation. Furthermore, should the plate 32 be transparent, then the radiation will pass therethrough into the chamber of body 10, thereby destroying contaminants on the brush handle.

FIG. 4 discloses a bracket 72 extending from the side wall of body member 10. The bracket 72 may be used to provide a wall mounted conditioner C. Should the conditioner C be wall mounted, then it may be desirable to provide an external jacket surrounding the body member 10 in order to prevent the user from peering into the conditioner C through the vent openings 36, and thereby being exposed to the ultraviolet radiation. Naturally, the jacket has a diameter exceeding that of the body member 10 and thereby acts as a flue so that the warmer air exiting from the conditioner C moves upwardly along the jacket interior surface.

OPERATION

Operation of the conditioner C is essentially automatic once the power supply is connected to a power source. Naturally, the user will set the digital clock upon initial installation, thereby automatically determining when the lamp 48 will be operated. As noted, the control device 52 automatically causes the lamp 48 to be illuminated, except in those instances when the cover member 12 is in the open position. Even then, should the cover member 12 be raised during a burn cycle, then operation of the lamp 48 will only be stopped for that period of time that the cover member 12 is raised, and will commence again as soon as the cover member 12 is lowered.

The user need merely pivot the cover member 12 into the open position of FIG. 2 in order to insert a toothbrush into the conditioner C. As previously noted, the brush is initially lowered through the opening 34 and is aligned with one of the straight portions 62. The brush is then moved radially until the respective enlarged portion 64 is reached, at which point the brush is rotated. The brush is then supported by the adjacent portions of the cover plate 32, thereby appropriately positioning the brush for conditioning. The cover member 12 is then closed, thereby permitting the control device 52 to operate the lamp 48 as specified by the circuitry.

Subsequent use of the conditioned toothbrush is easily accomplished by pivoting of the cover member 12 into the opened position. This pivoting moves the lamp 48 out of the chamber area. The user may then grasp the appropriate toothbrush without fear of burning his hand on the lamp 48. The brush, when grasped, need merely be rotated so that the handle thereof may be caused to pass through the respective straight portion 62, and ultimately removed through the central opening 34. The cover member 12 may then again be closed so that any other remaining toothbrushes may be conditioned, as dictated by the control circuit 52.

The reward circuit and speaker of FIG. 5 are appropriate for conditioners C directed towards children. In that instance, the speaker to plays a particular message when the cover membeer 12 is lifted. Likewise, the speaker to plays a particular message when the cover member 12 is again closed. The messages acknowledge and encourage the use of the conditioner C by the child, and implicitly use of the toothbrush.

While this invention has been described as having a preferred design, it is understood that it is capable of further modifications, uses and/or adaptations of the invention following in general the principle of the invention and including such departures from the present disclosure as come within known or customary practice in the art to which the invention pertains, and as may be applied to the central features hereinbefore set forth and fall within the scope of the invention of the limits of the appended claims.

What I claim is:

1. A toothbrush conditioning device, comprising:
   (a) a body member having an upper end;
   (b) a cover member;
   (c) said cover member having a first orientation mounted to said upper end for forming with said cover member a conditioning chamber and a second orientation remote from said upper end for providing access to said body member;
   (d) said body member including means for selectively positioning within the chamber a toothbrush to be conditioned;
   (e) toothbrush conditioning means disposed proximate the toothbrush to be conditioned when said cover member is in said first orientation for sterilizing the toothbrush;
   (f) control means operably associated with said conditioning means for causing automatic intermittent operation of said conditioning means when said cover member is in said first orientation; and
   (g) switch means operably associated with said cover member, said body member and said control means for permitting operation of said control means and said conditioning means when said cover member is in said first orientation and for preventing operation thereof when said cover member is in said second orientation.

2. A toothbrush conditioning device as in claim 1, wherein:
   (a) said switch means is disposed proximate said upper end and is engageable with said cover member when said cover member is in said first orientation.

3. A toothbrush conditioning device as in claim 2, wherein:
(a) said cover member has a lower end portion and said lower end portion is engageable with said switch means.

4. A toothbrush conditioning device as in claim 1, wherein:
(a) said control means includes timer means for causing operation of said conditioning means for a preselected duration.

5. A toothbrush conditioning device as in claim 1, wherein:
(a) said conditioning means includes an ultra-violet lamp.

6. A toothbrush conditioning device as in claim 1, wherein:
(a) said positioning means includes an apertured surface and a portion of said conditioning means extends downwardly beyond said surface when said cover member is in said first orientation.

7. A toothbrush conditioning device as in claim 6, wherein:
(a) said surface has a plurality of apertures and one of said apertures is centrally disposed; and
(b) said portion extends through said central aperture.

8. A toothbrush conditioning device as in claim 7, wherein:
(a) the other ones of said apertures are disposed circumferentially about the central aperture.

9. A toothbrush conditioning device as in claim 8, wherein:
(a) said switch means is radially outwardly spaced from the central aperture.

10. A toothbrush conditioning device as in claim 6, wherein:
(a) said conditioning means includes a radiant lamp; and
(b) at least a portion of said apertured surface is transparent to the radiation emitted by said lamp.

11. A toothbrush conditioning device as in claim 1, wherein:
(a) said cover member includes means for maintaining said cover member in said first orientation.

12. A toothbrush conditioning device as in claim 1, wherein:
(a) said control means is operably mounted within said cover member.

13. A toothbrush conditioning device as in claim 1, wherein:
(a) said conditioning means is centrally positioned within the chamber.

14. A toothbrush conditioning device as in claim 1, wherein:
(a) said body and cover members are each cylindrical.

15. A toothbrush conditioning device as in claim 14, wherein:
(a) each of said body and cover members has a substantially uniform external diameter.

16. A toothbrush conditioning device as in claim 1, and further comprising:
(a) reward means operably associated with said control means for acknowledging use of the device.

17. A toothbrush conditioning device as in claim 4, wherein:
(a) said timer means includes a digital clock.

18. A toothbrush conditioning device comprising:
(a) a cylindrical body member having an upper end;
(b) a cylindrical cover member;
(c) said cover member having a first orientation mounted to said upper end for forming with said body member a conditioning chamber and a second orientation remote from said upper end for providing access to said body member;
(d) means for maintaining said cover member in said first orientation;
(e) said body member including means for selectively positioning within the chamber at a desired elevation a toothbrush to be conditioned;
(f) an ultraviolet lamp disposed within the chamber and proximate the toothbrush to be conditioned when said cover is in said first orientation for sterilizing the toothbrush;
(g) control means operably associated with said lamp for causing automatic intermittent operation of said lamp when said cover member is in said first orientation; and
(h) switch means operably associated with said body member and said control means and engageable with said cover member for permitting operation of said control means and of said lamp when said cover member is in said first orientation and for preventing operation thereof when said cover member is in said second orientation.

19. A toothbrush conditioning device as in claim 18, wherein:
(a) said switch means has a portion extending beyond said upper end.

20. A toothbrush conditioning device as in claim 18, wherein:
(a) said control means includes timer means for causing operation of said lamp for a preselected duration.

21. A toothbrush conditioning device as in claim 18, wherein:
(a) said positioning means includes an apertured surface and a portion of said lamp extends downwardly beyond said surface when said cover member is in said first orientation.

22. A toothbrush conditioning device as in claim 21, wherein:
(a) said surface has a plurality of apertures and one of said apertures is centrally disposed; and
(b) said portion extends through the central aperture.

23. A toothbrush conditioning device as in claim 22, wherein:
(a) the other ones of said apertures are disposed circumferentially about the central aperture.

24. A toothbrush conditioning device as in claim 22, wherein:
(a) said switch means is radially outwardly spaced from the central aperture.

25. A toothbrush conditioning device as in claim 21, wherein:
(a) at least a portion of said surface is transparent to the radiation emitted by said lamp.

26. A toothbrush conditioning device as in claim 18, wherein:
(a) said control means is operably mounted within said cover member.

27. A toothbrush conditioning device as in claim 18, wherein:
(a) said body and cover members each has a substantially uniform external diameter, and the external diameter of said body member is substantially equal to the external diameter of said cover member.

* * * * *